US012605040B2

(12) United States Patent
Gaarde et al.

(10) Patent No.: US 12,605,040 B2
(45) Date of Patent: *Apr. 21, 2026

(54) WIRELESS SCANNING DEVICE

(71) Applicant: 3SHAPE A/S, Copenhagen K (DK)

(72) Inventors: Anders Gaarde, Søborg (DK); Kasper Krogh Hansen, Copenhagen Ø (DK)

(73) Assignee: 3Shape A/S, Kobenhavn K (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/916,843

(22) Filed: Oct. 16, 2024

(65) Prior Publication Data

US 2025/0031945 A1    Jan. 30, 2025

Related U.S. Application Data

(63) Continuation of application No. 17/422,875, filed as application No. PCT/EP2019/085179 on Dec. 13, 2019, now Pat. No. 12,144,486.

(30) Foreign Application Priority Data

Jan. 15, 2019    (EP) .................................... 19151924

(51) Int. Cl.
*G01B 11/25* (2006.01)
*A61B 1/00* (2006.01)
(Continued)

(52) U.S. Cl.
CPC ...... *A61B 1/00016* (2013.01); *A61B 1/00009* (2013.01); *A61B 1/00172* (2013.01); *A61B 1/227* (2013.01); *A61B 1/24* (2013.01)

(58) Field of Classification Search
CPC ........... A61B 1/00016; A61B 1/00009; A61B 1/00172; A61B 1/227; A61B 1/24;
(Continued)

(56) References Cited

U.S. PATENT DOCUMENTS 7,717,708 B2 * 5/2010 Sachdeva ............... G16H 50/50
433/24
9,262,864 B2 2/2016 Rohaly et al.
(Continued)

FOREIGN PATENT DOCUMENTS

CN    105096372 A    11/2015
CN    108476352 A    8/2018
(Continued)

OTHER PUBLICATIONS

International Search Report (PCT/ISA/210) and Written Opinion (PCT/ISA/237) mailed on Apr. 6, 2020, by the European Patent Office as the International Searching Authority for International Application No. PCT/EP2019/085179.

*Primary Examiner* — Howard D Brown, Jr.
(74) *Attorney, Agent, or Firm* — BUCHANAN INGERSOLL & ROONEY PC

(57)    ABSTRACT

The present disclosure provides a wireless scanning device, including a scanning housing, including an image detector configured for acquiring 2D-images at a first 2D-frame-rate; and one or more processor(s) coupled to the image detector such that the 2D-images can be processed by the processor(s) to form processed data; a wireless module being coupled to the processor(s) such that the wireless module receives the processed data from the processor(s) and wirelessly transmits the processed data.

17 Claims, 4 Drawing Sheets

(51) Int. Cl.
    *A61B 1/227*         (2006.01)
    *A61B 1/24*          (2006.01)

(58) Field of Classification Search
    CPC ............ A61B 1/00006; A61B 1/00011; A61B
            1/00032; A61B 1/00036; A61B 1/00042;
            A61B 1/00194; A61B 1/045; A61B
                              1/00108
    See application file for complete search history.

(56)             References Cited

U.S. PATENT DOCUMENTS

| | | |
|---|---|---|
| 11,122,255 B2 | 9/2021 | Fei et al. |
| 2006/0058652 A1 | 3/2006 | Little |
| 2007/0135680 A1 | 6/2007 | Mizuno |
| 2014/0248576 A1* | 9/2014 | Tchouprakov ....... A61C 9/0073 |
| | | 433/29 |
| 2015/0348226 A1 | 12/2015 | Vaishampayan et al. |
| 2016/0015368 A1 | 1/2016 | Poland |
| 2016/0256245 A1* | 9/2016 | Van Der Poel .... A61B 1/00177 |
| 2016/0327779 A1 | 11/2016 | Hillman |
| 2017/0195654 A1 | 7/2017 | Powers et al. |
| 2017/0296043 A1 | 10/2017 | On |
| 2018/0296080 A1* | 10/2018 | Glinec ..................... A61B 1/24 |
| 2019/0029522 A1* | 1/2019 | Sato .......................... G06T 7/75 |
| 2019/0104922 A1* | 4/2019 | Kasumi ............. A61B 1/00029 |
| 2019/0376784 A1* | 12/2019 | Tewes .................... G01B 11/24 |
| 2021/0128281 A1* | 5/2021 | Peleg ...................... A61B 1/24 |
| 2022/0061632 A1 | 3/2022 | Gaarde et al. |

FOREIGN PATENT DOCUMENTS

| | | |
|---|---|---|
| EP | 3402186 A1 | 11/2018 |
| JP | 2008284160 A | 11/2008 |
| KR | 101810917 B1 | 12/2017 |
| WO | 2015183585 A1 | 12/2015 |

\* cited by examiner

WIRELESS SCANNING DEVICE

CROSS-REFERENCE TO RELATED APPLICATIONS

The present application is a continuation of U.S. patent application Ser. No. 17/422,875, filed on Jul. 14, 2021, which is a U.S. National Stage of International Application No. PCT/EP2019/085179, filed on Dec. 13, 2019, which claims the benefit of European Patent Application No. EP 19151924.8, filed on Jan. 15, 2019. The entire contents of each of U.S. patent application Ser. No. 17/422,875, International Application No. PCT/EP2019/085179, and European Application No. EP 19151924.8 are hereby incorporated herein by reference in their entirety.

FIELD OF THE INVENTION

The present disclosure relates generally to a wireless scanning device. More specifically, the present disclosure relates to a wireless scanning device that manages power consumption and/or of heating. Most specifically, the present disclosure relates to a wireless scanning device for intraoral scanning and/or intra-ear scanning.

BACKGROUND

Management of power consumption and/or of heating is well-known in the art of computing devices, such as in computers and/or 3D scanning devices. For example, as is known in laptops, battery power is conserved by a technique called Central Processing Unit (CPU) throttling or dynamic frequency scaling, where the clock speed of the CPU is automatically adjusted. In other words, the laptop is slowed down to conserve the battery power. It is also known that adjusting the clock speed of the CPU can be based on the amount of heat that the CPU is generating. For example, if the CPU is too hot, i.e. overheated, the clock speed is reduced, and consequently the CPU is cooled. Such a technique may be called thermal throttling, being a specific technique within the field of CPU throttling.

Various other techniques within CPU throttling and even within thermal throttling are known. For example, within thermal throttling, it is known that processes to be run by a CPU or a Graphical Processing Unit (GPU) can be organized based on the temperature of the CPU. Other techniques than throttling a processor for reducing power consumption are also known. Examples are by reducing the power or process of a light projector, and/or by reducing the duty cycle of a light projector or an image detector. Power management of battery-powered devices is thus known in great details.

However, for wireless devices, such as for example wireless cameras, where images are transferred wirelessly, it is known that wireless transmission requires more power than wired transmission. The typical solution to provide more power to a wireless device is to switch the source of power, for example by switching from a battery to a wired power supply. Accordingly, there is a need for better power management of wireless devices, particularly wireless scanning devices.

SUMMARY

One object of the present disclosure is to provide a wireless scanning device that better manages power and/or heat such that no cable needs to be provided.

In one aspect of the invention, there is provided a wireless scanning device for providing data for a 3D-model of an object, comprising: a scanning housing, comprising: an image detector configured for acquiring 2D-images at a first 2D-frame-rate; and one or more processor(s) coupled to the image detector such that the 2D-images can be processed by said processor(s) to form processed data; a wireless module being coupled to said processor(s) such that the wireless module receives the processed data from said processor(s) and wirelessly transmits the processed data, wherein the processed data is the data for a 3D-model of the object.

The scanning device is preferably configured for being switched between two pre-defined scanning-operation-modes: a standard-mode, wherein the wireless module receives the processed data at a first data-rate defined by said processor(s); and a non-standard-mode, wherein the wireless module receives the processed data at a second data-rate defined by said processor(s).

It is advantageous that the wireless module in the preferred embodiment receives the processed data in the two different data-rates as above described, because once in non-standard-mode, the wireless module may in a further preferred embodiment receive less processed data than in the standard-mode, whereby the wireless module itself produces much less heat than in the standard-mode.

The inventors of the present scanning device have realized that the wireless module is responsible for producing much heat in a wireless scanning device, and therefore by limiting the processed data to the wireless module, the inventors have seen a dramatic decrease in temperature. A decrease in temperature of around 10% has been observed using the present invention, i.e. by switching from the standard-mode to the non-standard-mode.

The scanning device as here disclosed thus provides in one embodiment less generated heat and uses less power, so power is conserved.

Another object of the present disclosure is to provide a wireless scanning device that better manages power and/or heat such that more details of the scanned object is provided.

This can also be achieved using the scanning device as here disclosed. In another embodiment, the wireless module may receive more processed data than in the standard-mode, whereby the wireless module sends more processed data than in the standard-mode, and consequently a more precise 3D-model is able to be generated.

Accordingly, the inventors have realized that the wireless module is adaptable to a given scanning-operation-situation. In other words, in some embodiments, and if conditions allow the scanner to produce data, the scanning device can be switched from the standard-mode to the non-standard-mode.

The scanning device according to the present invention and for other embodiments provides more scanning details.

All in all, the present invention provides a wireless scanning device with greatly improved power and/or heat management.

BRIEF DESCRIPTION OF THE DRAWINGS

The above and/or additional objects, features and advantages of the present disclosure, will be further described by the following illustrative and non-limiting detailed description of embodiments of the present disclosure, with reference to the appended drawing(s), wherein.

DETAILED DESCRIPTION

Figure 1:
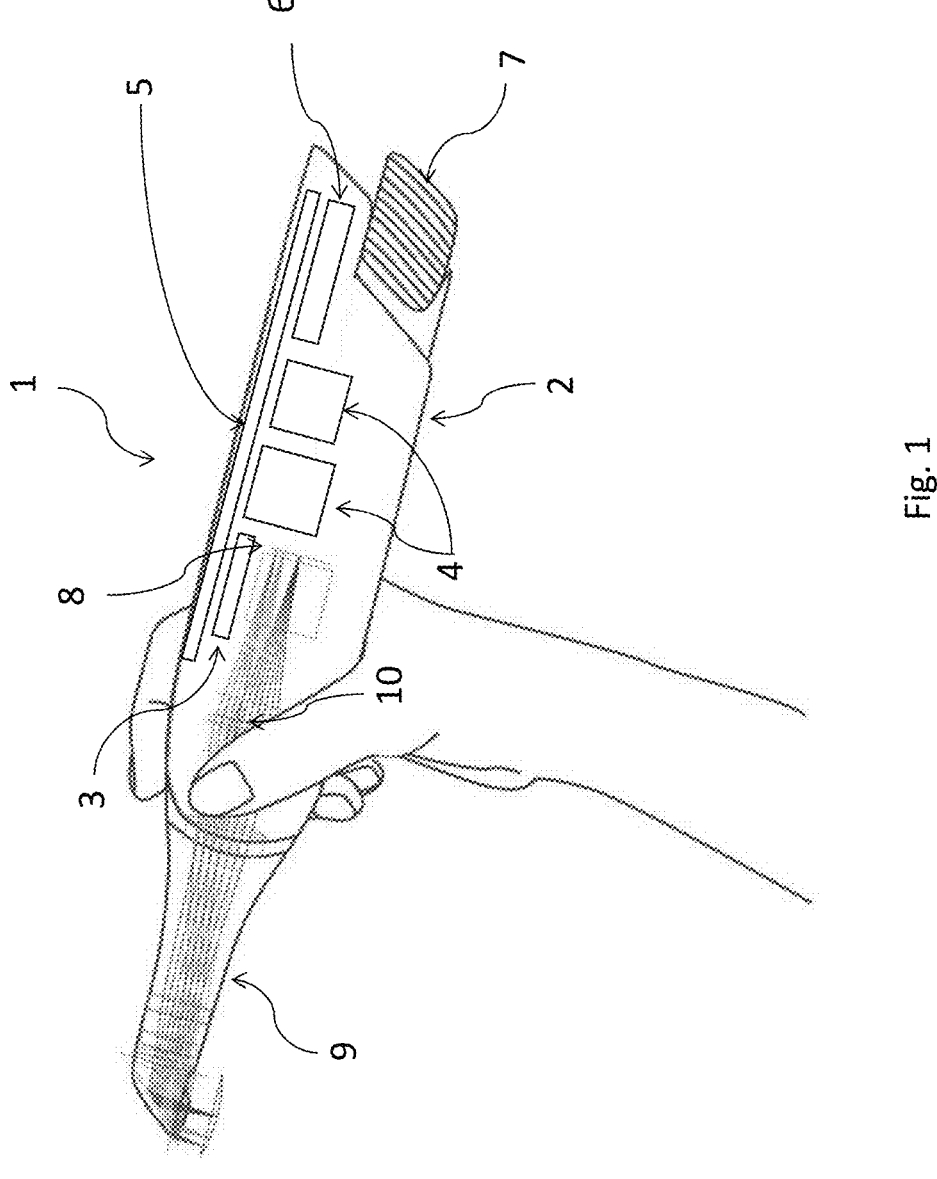
FIG. 1 shows an example of a wireless scanning device according to the invention.

A scanning device is different from a simple camera. A scanning device is, as also disclosed by the present invention, for providing data for a 3D-model of an object. A camera provides 2D-images, typically un-processed data, which is not related to a 3D model of an object. Scanning can be either active or passive, meaning that in active scanning, a light source is typically being used to project light onto the object, whereby the scanning device is able to derive surface-data from the light. Several techniques for active scanning are known in the field of scanning, for example:

triangularization scanning: where a projected pattern is projected on an object and imaged to an image detector such that based on the principle of triangularization, the depth information is derived, confocal scanning, where one ore more point sources are focused onto an object and imaged to an image detector such that based on the intensity of the imaged focus points, the depth information is derived, structured light illumination scanning, where a projected pattern is projected on an object and imaged to an image detector such that based on information of the pattern, the depth information is derived, interferometric scanning, where a pattern is projected on an object and imaged to an image detector through another pattern such that based on interference between the two patterns, the depth information is derived.

Passive scanning techniques are also known, where no light source is used. Such scanning techniques rely on information derivable from the images themselves. In some passive scanning devices, the image detector is not a standard image detector but may comprise for example an array of micro lenses.

Nevertheless, a camera, also known as a still-camera, provides 2D-images for displaying 2D-information of an object taken in a moment in time from one location in space, whereas a scanning device provides data for displaying 3D-information of an object taken over several moments in time and/or several locations in space.

Accordingly, a scanning device is much more power-demanding than a camera, and therefore a scanning device also produces much more heat than a camera.

Furthermore, as explained above, a scanning device also provides much more data than a camera, and to build a 3D-model, for example on an external computer, data needs to be transferred from the scanning device.

Typically for scanners, such data transfer is provided via wired data transfer, for example USB cables or Ethernet cables.

However, the scanning device according to the present invention comprises a wireless module being coupled to said processor(s) such that the wireless module receives the processed data from said processor(s) and wirelessly transmits the processed data, wherein the processed data is the data for the 3D-model of the object.

This allows the scanning device to be wireless, and in some embodiments, the scanning device according to the present invention is also battery-powered. This means that the scanning device can be operated without no cables at all. This is advantageous in scanning of for example a patient's teeth(s) or ear(s). The scanning device according to the invention is in one embodiment a handheld scanning device to be used in the field of dental scanning and/or in the field of hearing aid scanning. A handheld scanning device in the dental field is typically known as an intra-oral scanner. A handheld scanning device in the hearing aid field is typically known as an intra-ear scanner.

According to a preferred embodiment of the present invention, the scanning device is configured for being switched between two pre-defined operation-modes: a standard-mode, wherein the wireless module receives the processed data at a first data-rate defined by said processor(s); and a non-standard-mode, wherein the wireless module receives the processed data at a second data-rate defined by said processor(s).

The two pre-defined scanning-operation modes are according to their meaning two modes as have been defined prior use, i.e. the scanning-operation-modes have been programmed into the scanning device. There is thus a substantial difference between the two scanning-operation-modes, and the difference between the standard-mode and the non-standard mode is not just a consequence of the processor(s) becoming hot and/or a consequence of the processor(s) being slowed down by heat. In the preferred embodiment, the scanning device actively switches between the two scanning-operation modes, for example in an automatic manner. However, the switching may also be done in a manual manner, for example using a switch located on the scanning device and/or in a software related to the scanning device, for example on an external computer.

In relation to switching from the standard-mode to the non-standard mode, one embodiment is related to where the second data-rate is defined to be lower than the first data-rate, i.e. as pre-defined. There are several ways of providing such a lower second data-rate, and these embodiments, which will be called wireless-throttling-modes, will be described in the following. Various other embodiments of the scanning device will follow thereafter.

Wireless Throttling-Modes

In one embodiment, the non-standard-mode is provided by switching the first 2D-frame-rate to a second 2D-frame-rate, wherein the second 2D-frame-rate gets lower than the first 2D-frame-rate, whereby the second data-rate gets lower than the first data-rate, thereby defining the non-standard-mode as a wireless-throttling-mode. In this embodiment, the first 2D-frame-rate corresponds to a first pre-defined mode of the two pre-defined scanning-operation-modes, and the second 2D-frame-rate corresponds to a first pre-defined scanning-operation-mode of the two pre-defined scanning-operation-modes. The non-standard mode is defined as a wireless throttling-mode because it is the wireless module that is effectively throttled, i.e. the wireless module is changed to perform less than in the standard-mode. The wireless throttling-mode, i.e. the non-standard mode, is per definition a scanning-operation-mode, particularly because the scanning device acquires images at the pre-defined 2D-frame-rate. Accordingly, the standard-mode is also per definition a scanning-operation-mode. When the scanning device is changed to scan (i.e. acquire a plurality of images over time) at the pre-defined second 2D-frame-rate, the scanning device does not acquire as many 2D-images as in the standard-mode. In other words, the scanning device scans slower, and therefore, less data is acquired over time, less data is processed over time, and then less processed data is received over time by the wireless module. This has the effect that the wireless module is selected to use less power over the time and selected to produce less heat over the time. In this embodiment, because less data is acquired over time, a 3D-model is not being generated with as many details as in the standard-mode. However, the inventors have realized that a 3D model is still generated with enough details when operated at the non-standard-mode. The advantage of this embodiment, for example in comparison to typical CPU throttling, where the processor(s) is/are slowed down, is that the processor(s) is/are prevented from receiving some of the 2D-images that it would in the standard-mode. Thus, instead of providing the processor(s) with the same amount of data in the form of 2D-images, as is done in typical CPU-throttling, the processor(s) according to this embodiment is provided with less data to process. This effectively provides thermal cooling, or throttling, of the wireless module.

In another embodiment, the non-standard-mode is provided by maintaining the first 2D-frame-rate and shutting off the image detector for a specific time, whereby the second data-rate gets lower than the first data-rate, thereby defining the non-standard-mode as a wireless-throttling-mode. In this embodiment, the scanning device is not changed to scan (i.e. acquire a plurality of images over time) at a pre-defined second 2D-frame-rate. However, the result is the same as the previous embodiment—the scanning device does not acquire as many 2D-images as in the standard-mode. In other words, the scanning device scans slower, and therefore, less data is acquired over time, less data is processed over time, and then less processed data is received over time by the wireless module. This has the effect that the wireless module is selected to use less power over the time and selected to produce less heat over the time. In this embodiment, because less data is acquired over time, a 3D-model is not being generated with as much data as in the standard-mode. However, the inventors have realized that a 3D model is still generated with enough data when operated at the non-standard-mode. The advantage of this embodiment, for example in comparison to typical CPU throttling, where the processor(s) is/are slowed down, is that the processor(s) is/are prevented from receiving some of the 2D-images that it would in the standard-mode. Thus, instead of providing the processor(s) with the same amount of data in the form of 2D-images, as is done in typical CPU-throttling, the processor(s) according to this embodiment is provided with less data to process. This effectively provides thermal cooling, or throttling, of the wireless module.

In yet another embodiment, the non-standard-mode is provided by maintaining the first 2D-frame-rate and reducing the spatial resolution of the image detector for a specific time, whereby the second data-rate gets lower than the first data-rate, thereby defining the non-standard-mode as a wireless-throttling-mode. In this embodiment, the scanning device is not changed to scan (i.e. acquire a plurality of images over time) at a pre-defined second 2D-frame-rate. However, the result is the same as the previous embodiment—less data is acquired over time, less data is processed over time, and then less processed data is received over time by the wireless module. This has the effect that the wireless module is selected to use less power over the time and selected to produce less heat over the time. In this embodiment, because less data is acquired over time, a 3D-model is not being generated with as much data as in the standard-mode. However, the inventors have realized that a 3D model is still generated with enough data when operated at the non-standard-mode. The advantage of this embodiment, for example in comparison to typical CPU throttling, where the processor(s) is/are slowed down, is that the processor(s) is/are prevented from receiving some of the 2D-images that it would in the standard-mode. Thus, instead of providing the processor(s) with the same amount of data in the form of 2D-images, as is done in typical CPU-throttling, the processor(s) according to this embodiment is provided with less data to process. This effectively provides thermal cooling, or throttling, of the wireless module.

In a further embodiment, the non-standard-mode is provided by maintaining the first 2D-frame-rate and shutting off the wireless module for a specific time, whereby the wireless module receives the processed data at a second data-rate defined by said processor(s), thereby defining the non-standard-mode as a wireless-throttling-mode. In this embodiment, the scanning device is not changed to scan (i.e. acquire a plurality of images over time) at a pre-defined second 2D-frame-rate. Furthermore, the result may differ from the previous embodiments—the scanning device may acquire as many 2D-images as in the standard-mode, but the wireless module does not receive as much processed data as in the standard-mode. In other words, in this embodiment, the scanning device may scan indifferently from the standard-mode, and therefore, the same data is acquired over time, the same data is processed over time. However, less processed data is received over time by the wireless module. This also has the effect that the wireless module is selected to use less power over the time and selected to produce less heat over the time. In this embodiment, because less data is received over time, a 3D-model is not being generated with as much data as in the standard-mode. However, the inventors have realized that a 3D model is still generated with enough data when operated at the non-standard-mode. The advantage of this embodiment, for example in comparison to typical CPU throttling, where the processor(s) is/are slowed down, is that the wireless module is prevented from receiving some of the 2D-images that it would in the standard-mode. This effectively provides thermal cooling, or throttling, of the wireless module.

In further embodiments, the non-standard-mode is provided by maintaining the first 2D-frame-rate and guiding the processed data to another module for a specific time, whereby the wireless module receives the processed data at a second data-rate defined by said processor(s), thereby defining the non-standard-mode as a wireless-throttling-mode. In related embodiments, the other module may be a memory module or a storage module, for example configured to operate as a buffer, where processed data is buffered for the specific time. In this embodiment, the scanning device is not changed to scan (i.e. acquire a plurality of images over time) at a pre-defined second 2D-frame-rate. The result is however the same as the previous embodiment—the scanning device may acquire as many 2D-images as in the standard-mode, but the wireless does not receive as much processed data as in the standard-mode. In other words, in this embodiment, the scanning device may scan indifferently from the standard-mode, and therefore, the same data is acquired over time, the same data is processed over time. However, less processed data is received over time by the wireless module. This also has the effect that the wireless module is selected to use less power over the time and selected to produce less heat over the time. In this embodiment, because less data is received over time, a 3D-model is not being generated with as much data as in the standard-mode. However, the inventors have realized that a 3D model is still generated with enough data when operated at the non-standard-mode. The advantage of this embodiment, for example in comparison to typical CPU throttling, where the processor(s) is/are slowed down, is that the wireless module is prevented from receiving some of the 2D-images that it would in the standard-mode. This effectively provides thermal cooling, or throttling, of the wireless module.

Hyper-Mode

In some embodiments, the non-standard-mode is provided by switching the first 2D-frame-rate to a second 2D-frame-rate, wherein the second 2D-frame-rate gets higher than the first 2D-frame-rate, whereby the second data-rate gets higher than the first data-rate, thereby defining the non-standard-mode as a wireless-hyper-mode. The technical effect of such a mode is to provide more details of the object being scanned.

Conditional/Automatic Switching Between the Two Pre-Defined Scanning-Operation-Modes As previously described, switching between the two pre-defined scanning-operation-modes is preferably done in an automatic manner. In most embodiments, the switching is for example based on a condition. Several of such conditions are described in the following.

Temperature-Based Condition

In one embodiment, said being switched between at least two pre-defined scanning-operation-modes is based on a condition of said processor(s) and/or a part coupled to said processor(s). For example, the condition may be related to a temperature of said processor(s). The temperature may be provided by the processor(s) by for example on the request of temperature by a command to the processor(s). The processor(s) may therefore be configured to provide the condition of said processor(s). Additionally, and/or alternatively, the condition may be related to a part of the processor(s), for example the wireless module. Thus, in some embodiments, the condition may be related to the temperature of the wireless module.

In another embodiment, the scanning device further comprises a power supply unit being coupled to said processor(s). The power supply unit is preferably a battery. By providing power from a battery, the wireless scanning device becomes completely wireless, i.e. without wires for data-transmission, and without wires for power-transmission. This allows for scanning where the scanning device is not physically restricted in movement by a wire. Thus, a completely wireless scanning device is hereby provided, and this allows in some embodiments for better intra-oral and/or intra-ear scanning. When a power supply unit is coupled to said processor(s), the condition may be related to the temperature of the power supply unit.

In yet another embodiment, the scanning device further comprises a light source, for example a light source configured to project light onto the object being scanned. As previously described, a scanning device with a light source is known as relying on an active scanning technique. In a related embodiment, the light source is switched off at least for a period of time. This has the effect of both conserving power and producing less heat.

As described above, the temperature may be related to said processor(s), and/or related to the wireless module, and/or related to the scanning housing, and/or related to a power supply unit, and/or related to a light source.

In a preferred embodiment, the condition is a measure of a temperature in relation to a pre-defined temperature. For example, the condition may be defined as a situation where the measure of the temperature in relation to the pre-defined temperature defines that the measure of the temperature exceeds the pre-defined temperature, wherein the pre-defined temperature is a threshold.

In a related embodiment, the threshold is more than 60 degrees, preferably more than 70 degrees, more preferably around 78 degrees.

Power-Level Based Condition

In one embodiment, the condition is a measure of a power-level of a power supply unit in relation to a pre-defined power-level.

In another embodiment, the power-level is an absolute measure and/or a first derivative of the power-level with respect to time, and/or a second derivative of the power-level with respect to time.

Image-Based Condition

In one embodiment, the condition is based on the 2D-images received by said processor(s). For example, a quality parameter may be applied to the 2D-images, and if of a certain image quality, the scanning-operation-mode may be changed. For example, if the image quality is beyond a desired image quality, the scanning-operation mode might not need to be in standard-mode. The scanning device may then change the standard mode to a non-standard mode, such that when switched to the non-standard-mode, the first 2D-frame-rate is switched to a second 2D-frame-rate, wherein the second 2D-frame-rate gets lower than the first 2D-frame-rate.

In one example, in generation of a 3D-model, feedback may be provided to the scanning device about data density of the model in the apparent field-of-view of the scanning device. If the data density is higher than a specific threshold associated with data density and/or data quality, then the scanning device could switch to the non-standard mode, for example providing a low 2D-frame-rate. Alternatively, if the data density is lower than a specific threshold associated with data density and/or data quality, then the scanning device could switch to the non-standard mode, for example providing a high 2D-frame-rate.

Processor-Based, Image Detector-Based and Sensor-Based Conditions

In one embodiment, one or more external processor(s) is/are configured to provide the condition of said processor(s). For example, an external processor may execute a computer-implemented method for managing a frame-rate of a scanning device, comprising the steps of: transmitting instructions to inform an image detector to acquire 2D-images at a first 2D-frame-rate, whereby the scanning device operates in a standard-mode; receiving a condition of one or more processor(s) of the scanning device, and/or receiving a condition of a part coupled to said processor(s) of the scanning device; monitoring the condition to check whether or not the condition is full-filled such that: if the condition is not full-filled, then transmit instructions to inform the image detector to operate in a manner which prevents a wireless module in the scanning device from receiving the 2D-images at the first 2D-frame-rate, whereby the scanning device is switched to operate in a non-standard-mode; and if the condition is full-filled, then continue transmitting the instructions to inform the image detector to acquire 2D-images at the first 2D-frame-rate, whereby the scanning device continues to operate in the standard-mode.

In another embodiment, the scanning device further comprises a sensor configured to provide the condition. Such a sensor may be a temperature sensor.

Data-Transmission

In one embodiment, the scanning device is further configured such that when in standard-mode, the wireless module transmits the processed data at the first data-rate, and when in non-standard-mode, the wireless module transmits the processed data at the second data-rate.

Processed Data and Processing Rates

In a preferred embodiment, a ratio between the first data-rate and the first 2D-frame-rate is between 1:50 and 1:150, preferably between 1:80 and 1:120, most preferably around 1:90. For example, the first data-rate may be similar to a 3D-frame-rate, i.e. a collection of 2D-frames over time that together form a collection of 3D-frames over time. For examples, the image detector may in one embodiment acquire 2000 frames per second. Thus, in one second, the image detector acquires 2000 images. Out of theses 2000 images, there may be blocks of 20 images, each of such block forming a 3D-image. This corresponds to a situation where the 2D-first-frame rate is 2000 frames/images per second, and the corresponding 3D-frame-rate, here being equal to the first data-rate, is 20 frames/images per second.

In a most preferred embodiment, the first data-rate is identical to a 3D-frame-rate of more than 10 frames per second, more preferably between 10 and 30 frames per second, preferably more than 16 frames per second, most preferably around 20 frames per second.

In one embodiment, the processor(s) is/are configured to process data at the same rate as provided by the image processor. For example, in another or related embodiment, the first data-rate and/or the second data-rate correspond(s) to processing 2D-images provided to the processor(s) at an effective 2D-frame-rate between 1000 and 5000 frames per second, preferably between 1500 and 2500 frames per second, preferably between 1700 and 1900 frames per second, most preferably around 1800 frames per second. This may for example be provided by configuring the processor(s) to process data at the same data-rate as provided by the image detector. Also, the image detector may accordingly be set to acquire-2D images at a frame rate that is matched to the data-rate of the processor(s).

In a preferred embodiment, the second data-rate is less than 90% of the first data-rate, preferably is less than 80% of the first data-rate, more preferably is around 75% of the first data-rate. The effect of switching the data-rate to such rates is a dramatic decrease in power and/or heat production. Not only does it decrease power consumption and/or heat production of the processor(s), but also decreases the power consumption and/or heat production of the wireless module. The effect is thus a combined effect due to the wireless module being coupled to the processor(s).

As previously explained, the processed data may in most embodiment be in the form of 3D-data, for example 3D-images. The 3D-data may in some embodiments be a points cloud, for example with or without texture information. Thus, when in the standard-mode, said processor(s) generate (s) 3D-data at the first data-rate, and when in the non-standard-mode, said processor(s) generate(s) 3D-data at the second data-rate.

To process data into processed data, the processor(s) must be configured to do so. In most scanning devices, processing of data is performed on an external processor, for example located on a remote computer. The scanning device then only transmits data to be processed. Most scanning devices therefore do not have a processor to process data into processed data. As described in the beginning of the detailed description, depth information can be derived by several techniques. Each of these techniques therefore derive depth information by processing data. Some techniques are more processing-demanding than others. For example, deriving depth information from confocal scanning data is rather simple in comparison to structured light illumination scanning data. Depth information from confocal scanning only requires comparison of intensities with no or only little additional processing, whereas depth information from structured light illumination requires processing of the detected image and the projected pattern. However, if processing of data, for example to derive depth information and/or to generate 3D-data, can be performed on the scanning device, less data needs to be transmitted by the scanning device itself. Thus, to reduce the load of the wireless module, it is advantageous to process as much data as possible on the scanning device. Various processor(s) are known for processing data, but for rather simple processing, such as to compare intensities or more generally to perform operations such as multiplication and/or addition, a Field-Programmable Gate Array (FPGA) processor is desired. Thus, in a preferred embodiment, the processor(s) comprise (s) an FPGA-processor. In a more preferred embodiment, the processor(s) is configured for deriving depth information and/or for generating 3D-data. The 3D-data might not need to be in the distributed in the spatial domain. For example, the 3D-data may be partly in the spatial domain, and partly in the temporal domain. Further processing may then be applied to the 3D-data to convert the 3D-data to purely spatial domain-data. According to the invention, the processed data is the data for a 3D-model of the object, and as here explained, this may be 3D-data in the spatial domain or the temporal domain, or a mix thereof. Depth information is typically understood to be related to the case, where the 3D-data is in only the spatial domain.

To provide a wireless scanning device that is able to conserve power, the scanning device is preferably configured such that the wireless module transmits a low amount of data as possible. As just explained, implementation of a processor, such as an FPGA processor, where the processor is configured for deriving depth information and/or for generating 3D-data, means that the wireless module will transmit a low amount data.

In a most preferred embodiment, the processor(s) is further configured for compressing the processed data, such that the wireless module receives the processed data in the form of compressed data from said processor(s) and wirelessly transmits the processed data in the form of compressed data. Thus, in some embodiments, an FPGA processor both processes and compresses data.

According to the invention, the wireless module receives the processed data from said processor(s) and wirelessly transmits the processed data. For the wireless module to receive the processed data from said processor(s), said processor(s) must be configured to transmit the processed data to the wireless module. In one embodiment, the transmission of data to the wireless module is performed by said processer(s), preferably a central processing unit (CPU) comprising a reduced instruction set computer (RISC) architecture. For example, to transmit data to the wireless module, said processor(s) may be in the form of an Advanced RISC Machines (ARM)-processor such as based on 32 bits or 64 bits instructions. In other words, the processor(s) may comprise an ARM-processor. An ARM-processor is different from an FPGA processor, and the two types of processors are designed for different tasks. Thus, in most preferred embodiments, said processor(s) comprise both an FPGA-processor and an ARM-processor.

However, the inventors have realized that in a wireless scanning device using both an FPGA-processor and an ARM-processor together with a wireless module, power is rapidly consumed, and great amount of heat is produced.

It is therefore desirable in one embodiment to further limit the amount of heat produced and to limit the power consumed by both the processors and the wireless module. In one embodiment said processor(s) and wireless module are integrated in a programmable system on a chip (PSoC) such that a first part of said chip is adapted with hardware programmability and a second part of said chip is adapted with software programmability, wherein the first part is configured to form the processed data, and wherein the second part is configured to send the processed data to the wireless module.

In other words, the inventors have realized that to limit the amount of heat produced and to limit the power consumed by said processor(s) and the wireless module, a PSoC may be implemented in the scanning device, the PSoC being able to perform tasks as both defined by an FPGA-processor and an ARM-processor. A PSoC integrates the software programmability of an ARM-based processor with the hardware programmability of an FPGA.

In a related embodiment, the first part is further configured to form processed data in the form of compressed data.

Example 1—A Wireless Scanning Device

FIG. 1 shows an example of a wireless scanning device 1 according to the invention.

The wireless scanning device 1 for providing data for a 3D-model of an object comprises a scanning housing 2, comprising: an image detector 3 configured for acquiring 2D-images at a first 2D-frame-rate; one or more processor(s) 4 coupled to the image detector 3, here via a main printed circuit board (PCB) 5, such that the 2D-images can be processed by said processor(s) 4 to form processed data. The scanning device further comprises a wireless module 6 being coupled to said processor(s), here again via the main PCB 5, such that the wireless module 6 receives the processed data from said processor(s) 4 and wirelessly transmits the processed data, wherein the processed data is the data for a 3D-model of the object. Furthermore, the scanning device 1 is configured for being switched between two pre-defined scanning-operation-modes: a standard-mode, wherein the wireless module 6 receives the processed data at a first data-rate defined by said processor(s) 4; and a non-standard-mode, wherein the wireless module 6 receives the processed data at a second data-rate defined by said processor(s) 4. The scanning device 1 further comprises a power supply unit 7 being coupled to said processor(s) 4, here again via the main PCB 5. The power supply unit 7 is in this example a battery. Accordingly, the wireless scanning device is completely wireless and requires no power from an external power supply. As also shown in this example, this provides for a hand-held scanning device. The scanning device as shown here, also comprises a light source 8, here shown to project light (at various field of views) on an object, via a scanning tip 9. The scanning device is in this example configured as an intra-oral scanning device—the scanning tip 9 is able to be inserted into the mouth of a patient, such that for example teeth can be scanned. During scanning, a lens 10 inside the scanning housing 2 is moved back and forth.

Figure 2:
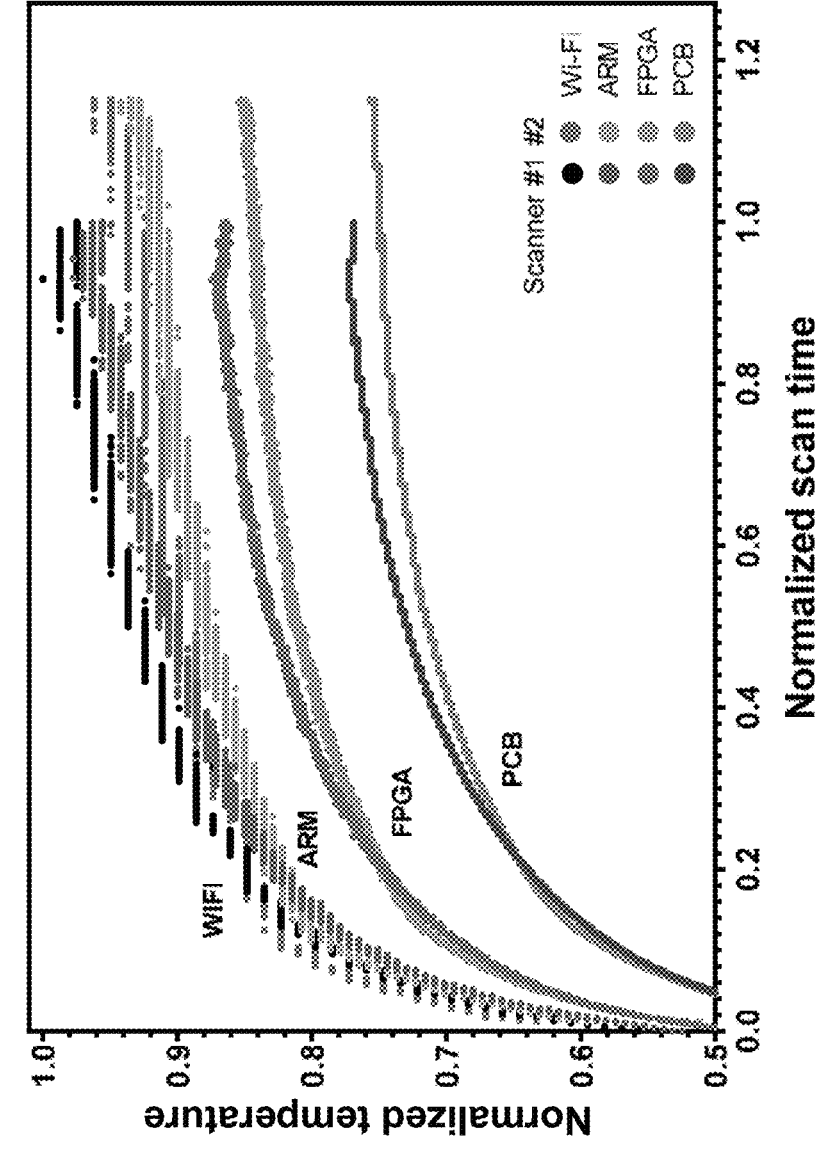
FIG. 2 shows an example of heat-generation in a scanning device 1 having two pre-defined scanning-operation-modes.

Example 2—Heat-Generation in a Scanning Device with Two Pre-Defined Scanning-Operation-Modes FIG. 2 shows an example of heat-generation in a scanning device 1 having two pre-defined scanning-operation-modes. The scanning device 1 is set up as a completely wireless scanning device 1, i.e. with a battery 7, similarly to the device shown in FIG. 1. The scanning device is configured for being switched between two pre-defined scanning-operation-modes: a standard-mode, wherein the wireless module receives the processed data at a first data-rate defined by said processor(s); and a non-standard-mode, wherein the wireless module receives the processed data at a second data-rate defined by said processor(s).

In the standard-mode, referred to as Scanner #1 in FIG. 2, the wireless module 6 receives the processed data at a first data-rate defined by said processor(s) 4. More specifically, the first data-rate correspond(s) to processing 2D-images provided to the processor(s) 4 at an effective 2D-frame rate around 1800 frames per second. In other words, the processor(s) is/are configured to process data at the same rate as provided by the image processor, here set to operate at around 1800 frames per second. The lens 10 as referred to in FIG. 1 is moved back and forth at 10 Hz (20 sweeps per second). A single sweep equals one 3D-image. For the processor(s) 4 to process a 3D scan (composed of several 2D-images), there is a trigger on the image detector 3 that must be armed. This arming is done continuously by a data service running on an external computer. In other words, the arming of the trigger on the image detector 3 defines the first data-rate, in this example set to 1800 frames per second. Thus, in this example, the first data-rate as defined by said processor(s) 4 is defined via the image detector 3, wherein the image detector is triggered by the external processor running on the external computer.

In the non-standard-mode, referred to as Scanner #2 in FIG. 2, the wireless module 6 receives the processed data at a second data-rate defined by said processor(s) 4. More specifically, the second data-rate correspond(s) to processing 2D-images provided to the processor(s) 4 at an effective 2D-frame rate that is lower than the first 2D-frame-rate, whereby the second data-rate gets lower than the first data-rate. In other words, the processor(s) is/are configured to process data at the same rate as provided by the image processor, here set to operate at around 1350 frames per second. The lens 10 as referred to in FIG. 1 is still moved back and forth at 10 Hz (20 sweeps per second). As for the standard-mode, a single sweep equals one 3D-image. For the processor(s) 4 to process a 3D scan (composed of several 2D-images), there is, similarly to the standard-mode, a trigger on the image detector 3 that must be armed. This arming is, similarly to the standard-mode, done continuously by a data service running on an external computer. In other words, the arming of the trigger on the image detector 3 defines the second data-rate, in this example set to 1350 frames per second. Thus, in this example, the second data-rate as defined by said processor(s) 4 is defined via the image detector 3, wherein the image detector is triggered by the external processor running on the external computer.

As can be deduced from this example, the second data-rate is pre-defined to be 75% of the first data-rate. As described above, the arming only takes place 75% of the time. In this manner, the image detector 3 is paused or switched off. In other words, and in relation to the lens movement, the image detector 3 is switched off every fourth sweep, meaning that an entire sweep is not processed and send to the computer. When the image detector 3 is off, the processor(s) do(es) not perform calculations on the images, and when no output is provided by the processor(s), no data is transferred to the wireless module. This is what reduces the heat over time on the wireless module as can be seen in FIG. 2. The normalized scan time is more approximately 30 minutes. The scanning device was first scanning in the standard-mode, and then scanning in the non-standardmode, while measuring the temperature of the different scanner components, where after the measuring results were aligned in time.

FIG. 2 shows not only the generated heat of the wireless module 6, but also shows heat-generation of other different internal scanner components. The other scanner components as shown in FIG. 2 are two processors, referred to as an ARM processor and an FPGA processor, both residing on a PCB.

In terms of heat-generation of all the components, it can be seen that in the two pre-defined modes, the WI-FI module produces more heat than the ARM processor, which produces more heat than the FPGA processor, which produces more heat than the PCB (Printed Circuit Board).

It is evident from FIG. 2 that the heat-generation of all the components is substantially lower for the non-standard-mode, referred to as "scanner #2", in comparison to the standard-mode, referred to as "Scanner #1".

In other words, FIG. 2 illustrates the impact on the heat-generation of all the components by operating the scanner in the two modes according to the invention. The quantified thermal impact of going from standard-mode to non-standard mode as described according to the invention is 3.2% lower temperature development of the PCB and FPGA processor and 5.1% lower temperature development for the ARM processor and WI-FI module.

Figure 3:
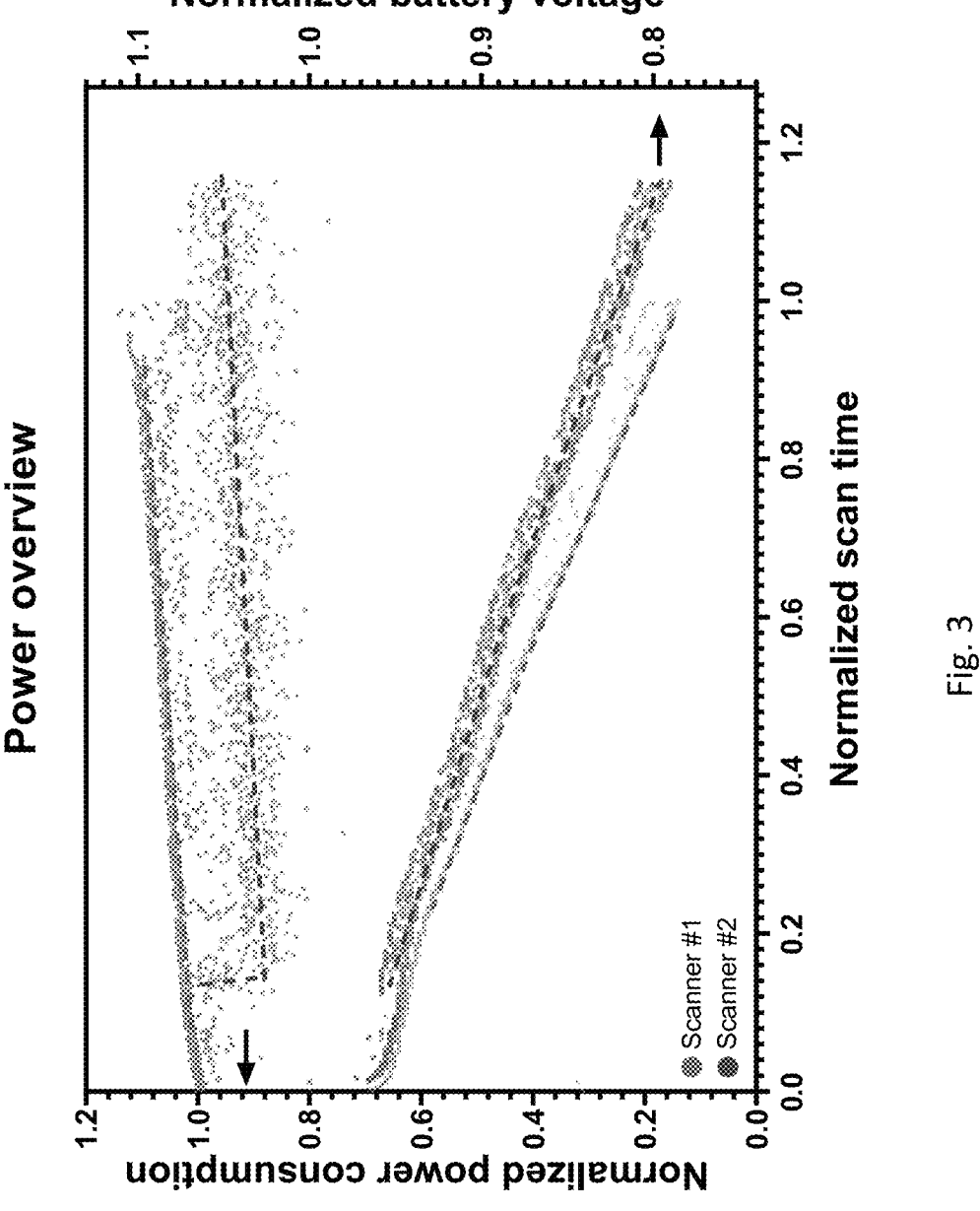
FIG. 3 shows an example of power-consumption in a scanning device 1 having two pre-defined scanning-operation-modes.

Example 3—Power Consumption in a Scanning Device with Two Pre-Defined Scanning-Operation-Modes FIG. 3 shows an example of power-consumption in a scanning device 1 having two pre-defined scanning-operation-modes. The scanning device 1 is set up as a completely wireless scanning device 1, i.e. with a battery 7, similarly to the device shown in FIG. 1. The scanning device is configured for being switched between two pre-defined scanning-operation-modes: a standard-mode, wherein the wireless module receives the processed data at a first data-rate defined by said processor(s); and a non-standard-mode, wherein the wireless module receives the processed data at a second data-rate defined by said processor(s).

In FIG. 3, the left y-axis displays the normalized power consumption of the scanner as a function of scan time, along the x-axis. The two-scanning-operation-modes are displayed in the chart. The red points represent the standard-mode, referred to as "scanner #1" and the blue data points represent the non-standard-mode, referred to as "scanner #2". The scanning device was first scanning in the standard-mode, and then scanning in the non-standard-mode, while measuring the power consumption, where after the measuring-results were aligned in time. From the power profiles of both scanning-modes, the modes start out with identical power consumption rate, but after a short period, scanner #2 impacts the power profile by an abrupt drop in power consumption, resulting in a parallel displacement relative to scanner #1. The power consumption when in non-standard-mode is 16.7% lower than that of the standard-mode.

In FIG. 3, the right y-axis shows the normalize power level of the battery in terms of voltage supplied from the battery 7. The battery-life in non-standard-mode is increased by 15.5% in comparison to standard-mode.

Figure 4:
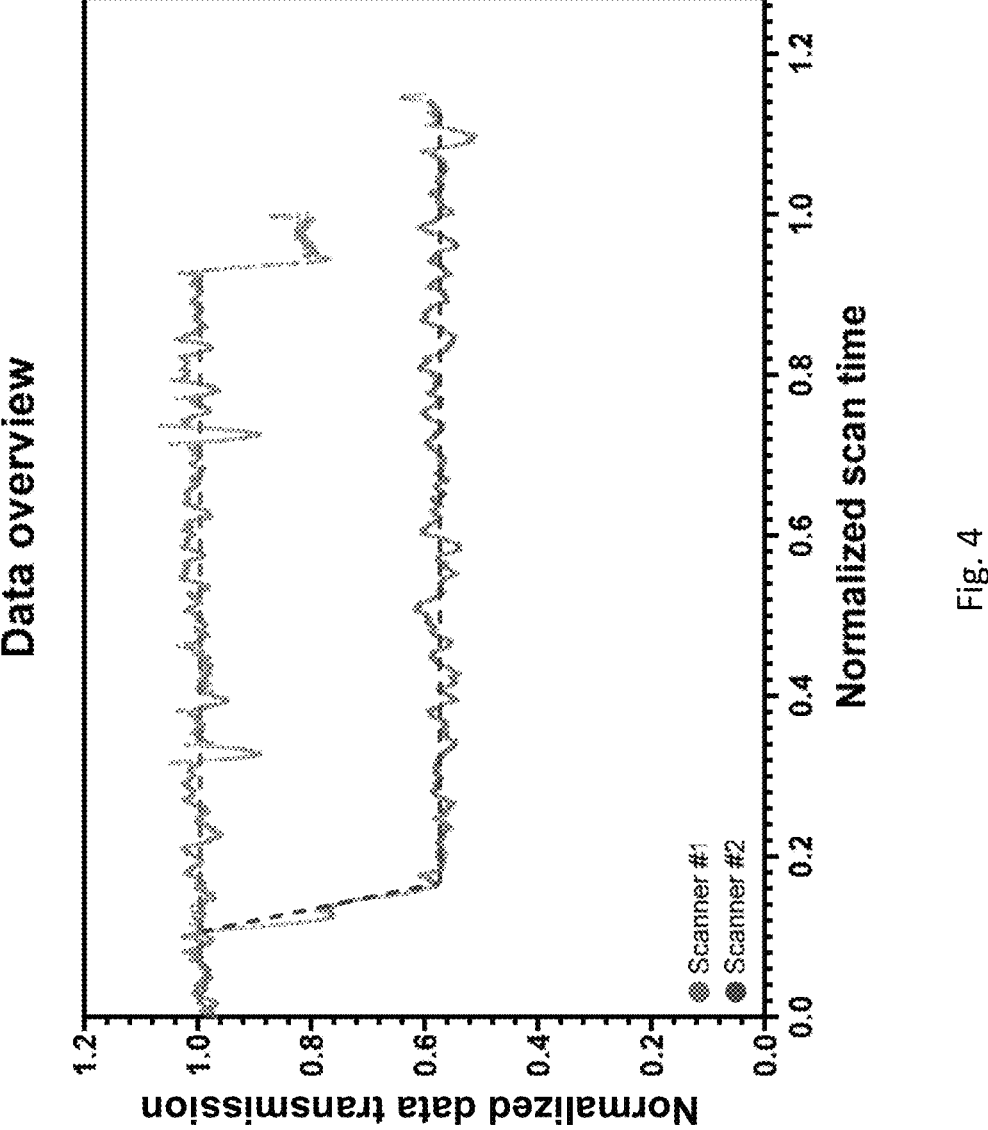
FIG. 4 shows an example of data-transmission in a scanning device 1 having two pre-defined scanning-operation-modes.

Example 4—Data Transmission in a Scanning Device with Two Pre-Defined Scanning-Operation-Modes FIG. 4 shows an example of data-transmission in a scanning device 1 having two pre-defined scanning-operation-modes. The scanning device 1 is set up as a completely wireless scanning device 1, i.e. with a battery 7, similarly to the device shown in FIG. 1. The scanning device is configured for being switched between two pre-defined scanning-operation-modes: a standard-mode, wherein the wireless module receives the processed data at a first data-rate defined by said processor(s); and a non-standard-mode, wherein the wireless module receives the processed data at a second data-rate defined by said processor(s).

In FIG. 4, the left y-axis displays the normalized data transmission of the wireless module in the scanner as a function of scan time, along the x-axis. The two-scanning-operation-modes are displayed in the chart. The red points represent the standard-mode, referred to as "scanner #1" and the blue data points represent the non-standard-mode, referred to as "scanner #2". The scanning device was first scanning in the standard-mode, and then scanning in the non-standard-mode, while measuring the data transmission, where after the measuring-results were aligned in time. From the data transmission profiles of both scanning-modes, the modes start out with identical data transmission rates, but after a short period, scanner #2 impacts the data transmission profile by an abrupt drop in transmission, resulting in a parallel displacement relative to scanner #1. The data transmission when in non-standard-mode is 57.2% lower than that of the standard-mode.

Example 5—a Scanning Device with Two Pre-Defined Scanning-Operation-Modes

In this example, a scanning device according to the invention is configured for being switched between two pre-defined scanning-operation-modes: a standard-mode, wherein the wireless module receives the processed data at a first data-rate defined by said processor(s); and a non-standard-mode, wherein the wireless module receives the processed data at a second data-rate defined by said processor(s). The scanning device as described in this example comprises a moving lens 10 which moves back and forth during scanning.

During a focus lens sweep, the lens 10 is accelerated from its initial position to its top speed and deaccelerated as it comes to rest at its end position. This motion is repeated as the lens is moved back and forth.

Each time the lens 10 has traveled a full length is referred to as a 'sweep'. During the focus lens sweep, the image detector 3 is acquiring 2D images with a constant frame-rate of for example 1800 frames or second (fps). This defines the first data-rate.

As the lens is traveling with a varying speed, the image density i.e. number of 2D-images pr. mm focus depth is not uniform. A relative high number of 2D-images is acquired within a narrow depth interval near the end positions of the focus lens during a sweep.

In such a case, the second data-rate can be obtained by discarding the 2D-images near the end positions of the focus lens movement span. This would not affect the overall 3D images frame rate, but each sub scan would contain slightly less 3D-information.

By applying encoder feedback from the lens position system to control software of the image detector, the image detector is switched off at the end-positions, thereby lowering the duty-cycle of the image detector, the processor(s) and the wireless module.

If the focus lens is considered as a simple harmonic oscillator, more than 20% of the images is acquired within 6% of the focus sweep length. Thus, by reducing the focus-sweep length by 6%, 20% less images need to be recorded by the image detector, and 20% less images need to be processed by the processor(s), whereby the wireless module receives less processed data.

Example 6—a Scanning Device with Two Pre-Defined Scanning-Operation-Modes

In this example, a scanning device according to the invention is configured for being switched between two pre-defined scanning-operation-modes: a standard-mode, wherein the wireless module receives the processed data at a first data-rate defined by said processor(s); and a non-standard-mode, wherein the wireless module receives the processed data at a second data-rate defined by said processor(s). The scanning device is acquiring 3D data and/or color information based on projecting a sequence of projected patterns and capturing the reflected light by one or more image detectors.

In this example, second data-rate is achieved by changing the number of projected patterns and/or the illumination period of each pattern (exposure time) within the sequence for generating a 3D frame.

By decreasing the number of patterns projected by skipping some of the coded patterns, the entire 3D frame capturing sequence gets shorter, resulting in reduced data-rate of at least the processor(s).

Further details are provided by the following items.

Items

1. A wireless scanning device for providing data for a 3D-model of an object, comprising:
   a scanning housing, comprising:
      an image detector configured for acquiring 2D-images at a first 2D-frame-rate;
      one or more processor(s) coupled to the image detector such that the 2D-images can be processed by said processor(s) to form processed data;
      a wireless module being coupled to said processor(s) such that the wireless module receives the processed data from said processor(s) and wirelessly transmits the processed data,
      wherein the processed data is the data for a 3D-model of the object,
   wherein the scanning device is configured for being switched between two pre-defined scanning-operation-modes:
      a standard-mode, wherein the wireless module receives the processed data at a first data-rate defined by said processor(s); and
      a non-standard-mode, wherein the wireless module receives the processed data at a second data-rate defined by said processor(s).
2. The wireless scanning device according to item 1, wherein the non-standard-mode is provided by switching the first 2D-frame-rate to a second 2D-frame-rate, wherein the second 2D-frame-rate gets lower than the first 2D-frame-rate, whereby the second data-rate gets lower than the first data-rate, thereby defining the non-standard-mode as a wireless-throttling-mode.
3. The wireless scanning device according to item 1, wherein the non-standard-mode is provided by maintaining the first 2D-frame-rate and shutting off the image detector for a specific time, whereby the second data-rate gets lower than the first data-rate, thereby defining the non-standard-mode as a wireless-throttling-mode.
4. The wireless scanning device according to item 1, wherein the non-standard-mode is provided by maintaining the first 2D-frame-rate and reducing the spatial resolution of the image detector for a specific time, whereby the second data-rate gets lower than the first data-rate, thereby defining the non-standard-mode as a wireless-throttling-mode.
5. The wireless scanning device according to item 1, wherein the non-standard-mode is provided by maintaining the first 2D-frame-rate and shutting off the wireless module for a specific time, whereby the wireless module receives the processed data at a second data-rate defined by said processor(s), thereby defining the non-standard-mode as a wireless-throttling-mode.
6. The wireless scanning device according to item 1, wherein the non-standard-mode is provided by maintaining the first 2D-frame-rate and guiding the processed data to another module for a specific time, whereby the wireless module receives the processed data at a second data-rate defined by said processor(s), thereby defining the non-standard-mode as a wireless-throttling-mode.
7. The wireless scanning device according to any of the preceding items, wherein the first data-rate and/or the second data-rate correspond(s) to processing 2D-images provided to the processor(s) at an effective 2D-frame rate between 1000 and 5000 frames per second, preferably between 1500 and 2500 frames per second, preferably between 1700 and 1900 frames per second, most preferably around 1800 frames per second.
8. The wireless scanning device according to any of the preceding items, wherein the second data-rate is less than 90% of the first data-rate, preferably is less than 80% of the first data-rate, more preferably is around 75% of the first data-rate.
9. The wireless scanning device according to any of the previous items, wherein the processed data is in the form of 3D-data such that when in the standard-mode, said processor(s) generate(s) 3D-data at the first data-rate, and when in the non-standard-mode, said processor(s) generate(s) 3D-data at the second data-rate.
10. The wireless scanning device according to item 1, wherein the non-standard-mode is provided by switching the first 2D-frame-rate to a second 2D-frame-rate, wherein the second 2D-frame-rate gets higher than the first 2D-frame-rate, whereby the second data-rate gets higher than the first data-rate, thereby defining the non-standard-mode as a wireless-hyper-mode.
11. The wireless scanning device according to any of the previous items, wherein said being switched between at least two pre-defined operation-modes is based on a condition of a said processor(s) and/or a part coupled to said processor(s).
12. The wireless scanning device according to item 11, wherein the condition is a measure of a temperature in relation to a pre-defined temperature.
13. The wireless scanning device according to item 12, wherein the temperature is related to said processor(s), and/or related to the wireless module, and/or related to the scanning housing, and/or related to a power supply unit, and/or related to a light source.
14. The wireless scanning device according to item 12, wherein the condition is defined as a situation where the measure of the temperature in relation to the pre-defined temperature defines that the measure of the temperature exceeds the pre-defined temperature, wherein the pre-defined temperature is a threshold.

15. The wireless scanning device according to item 12, wherein the threshold is more than 60 degrees, preferably more than 70 degrees, more preferably around 78 degrees.

16. The wireless scanning device according to item 11, wherein the condition is a measure of a power-level of a power supply unit in relation to a pre-defined power-level.

17. The wireless scanning device according to item 16, wherein the power-level is an absolute measure and/or a first derivative of the power-level with respect to time, and/or a second derivative of the power-level with respect to time.

18. The wireless scanning device according to item 11, wherein the condition is based on the 2D-images received by said processor(s).

19. The wireless scanning device according to item 11, wherein said processor(s) is/are configured to provide the condition of said processor(s).

20. The wireless scanning device according to item 11, wherein one or more external processor(s) is/are configured to provide the condition of said processor(s).

21. The wireless scanning device according to item 11, wherein the scanning device further comprises a sensor configured to provide the condition.

22. The wireless scanning device according to any of the previous items, wherein the scanning device is further configured such that when in standard-mode, the wireless module transmits the processed data at the first data-rate, and when in non-standard-mode, the wireless module transmits the processed data at the second data-rate.

23. The wireless scanning device according to any of the previous items, wherein said processor(s) and wireless module are integrated in a programmable system on a chip such that a first part of said chip is adapted with hardware programmability and a second part of said chip is adapted with software programmability, wherein the first part is configured to form the processed data, and wherein the second part is configured to send the processed data to the wireless module.

24. The wireless scanning device according to item 22, wherein the first part is further configured to form processed data in the form of compressed data.

25. The wireless scanning device according to any of the previous items, wherein the scanning device is an intra-oral scanning device and/or an intra-ear scanning device.

The invention claimed is:

1. A wireless scanning device for providing data for a 3D-model of an object, comprising:
   a scanning housing, comprising:
   an image detector configured for acquiring 2D-images at a first 2D-frame-rate;
   one or more processor(s) coupled to the image detector such that the 2D-images can be processed by said processor(s) to form processed data;
   a power supply unit that includes a battery;
   a wireless module coupled to said processor(s) such that the wireless module receives the processed data from said processor(s) and wirelessly transmits the processed data;

wherein the processed data is data for a 3D-model of the object,
   wherein the scanning device is configured for being switched between two pre-defined scanning-operation-modes, wherein switching between the at least two pre-defined scanning operation-modes is based on a condition, wherein the condition is a measure of a power-level of the power supply unit in relation to a pre-defined power-level, and the power-level is an absolute measure and/or a first derivative of the power-level with respect to time, and/or a second derivative of the power-level with respect to time, wherein the pre-defined scanning-operation modes are as follows:
   a standard-mode, wherein the wireless module receives the processed data at a first data-rate defined by said processor(s); and
   a non-standard-mode, wherein the wireless module receives the processed data at a second data-rate defined by said processor(s),
   wherein the non-standard-mode is provided by shutting off the image detector for a specific time, whereby the second data-rate gets lower than the first data-rate, thereby defining the non-standard-mode as a wireless-throttling-mode.

2. The wireless scanning device according to claim 1, wherein the non-standard-mode is provided by switching the first 2D-frame-rate to a second 2D-frame-rate, wherein the second 2D-frame-rate gets lower than the first 2D-frame-rate, whereby the second data-rate gets lower than the first data-rate, thereby defining the non-standard-mode as a wireless-throttling-mode.

3. The wireless scanning device according to claim 1, wherein the non-standard-mode is provided by maintaining the first 2D-frame-rate and reducing the spatial resolution of the image detector for a specific time, whereby the second data-rate gets lower than the first data-rate, thereby defining the non-standard-mode as a wireless-throttling-mode.

4. The wireless scanning device according to claim 1, wherein the first data-rate or the second data-rate correspond(s) to processing 2D-images provided to the processor(s) at an effective 2D-frame rate between 1000 and 5000 frames per second.

5. The wireless scanning device according to claim 1, wherein the second data-rate is less than 90% of the first data-rate.

6. The wireless scanning device according to claim 1, wherein the processed data is in the form of 3D-data such that when in the standard-mode, said processor(s) generate(s) 3D-data at the first data-rate, and when in the non-standard-mode, said processor(s) generate(s) 3D-data at the second data-rate.

7. The wireless scanning device according to claim 1, wherein the scanning device is further configured such that when in standard-mode, the wireless module transmits the processed data at the first data-rate, and when in non-standard-mode, the wireless module transmits the processed data at the second data-rate.

8. The wireless scanning device according to claim 1, wherein said processor(s) and wireless module are integrated in a programmable system on a chip such that a first part of said chip is adapted with hardware programmability and a second part of said chip is adapted with software programmability, wherein the first part is configured to form the processed data, and wherein the second part is configured to send the processed data to the wireless module.

9. The wireless scanning device according to claim 1, wherein the first part is further configured to form processed data in the form of compressed data.

10. The wireless scanning device according to claim 1, wherein the scanning device is an intra-oral scanning device or an intra-ear scanning device.

11. The wireless scanning device according to claim 1, wherein the non-standard-mode is provided by maintaining the first 2D-frame-rate.

12. The wireless scanning device according to claim 1, wherein the first data-rate and/or the second data-rate correspond(s) to processing 2D-images provided to the processor(s) at an effective 2D-frame rate between 1500 and 2500 frames per second.

13. The wireless scanning device according to claim 1, wherein the first data-rate and/or the second data-rate correspond(s) to processing 2D-images provided to the processor(s) at an effective 2D-frame rate between 1700 and 1900 frames per second.

14. The wireless scanning device according to claim 1, wherein the first data-rate and/or the second data-rate correspond(s) to processing 2D-images provided to the processor(s) at an effective 2D-frame rate around 1800 frames per second.

15. The wireless scanning device according to claim 1, wherein the second data-rate is less than 80% of the first data-rate.

16. The wireless scanning device according to claim 1, wherein the second data-rate is around 75% of the first data-rate.

17. The wireless scanning device according to claim 1, wherein the first data-rate and the second data-rate correspond(s) to processing 2D-images provided to the processor(s) at an effective 2D-frame rate between 1000 and 5000 frames per second.

*     *     *     *     *